(12) United States Patent
Fujioka et al.

(10) Patent No.: US 6,512,811 B2
(45) Date of Patent: Jan. 28, 2003

(54) EVALUATION METHOD AND EVALUATION APPARATUS FOR SEMICONDUCTOR DEVICE

(75) Inventors: Hiroshi Fujioka, Tokyo (JP); Masaharu Oshima, Tokyo (JP)

(73) Assignee: Semiconductor Technology Academic Research Center, Kanagawa (JP)

( * ) Notice: Subject to any disclaimer, the term of this patent is extended or adjusted under 35 U.S.C. 154(b) by 0 days.

(21) Appl. No.: 10/068,104

(22) Filed: Feb. 5, 2002

(65) Prior Publication Data

US 2002/0131550 A1 Sep. 19, 2002

(30) Foreign Application Priority Data

Mar. 19, 2001 (JP) ........................................ 2001-078517

(51) Int. Cl.$^7$ ............................................... G01N 23/06
(52) U.S. Cl. ......................................................... 378/51
(58) Field of Search ............................................ 378/51

Primary Examiner—Craig E. Church
(74) Attorney, Agent, or Firm—Christensen O'Connor Johnson Kindness PLLC

(57) ABSTRACT

Evaluating electrical properties of a semiconductor device by measuring and analyzing a junction capacitance of a semiconductor provided in the semiconductor device and a transient change of the junction capacitance while applying an X-ray beam to the semiconductor device intermittently, and evaluating a structure and electron states of the semiconductor by measuring and analyzing an energy spectrum of an X-ray beam absorbed into an element present in the semiconductor while applying an X-ray beam to the semiconductor device continuously.

24 Claims, 11 Drawing Sheets

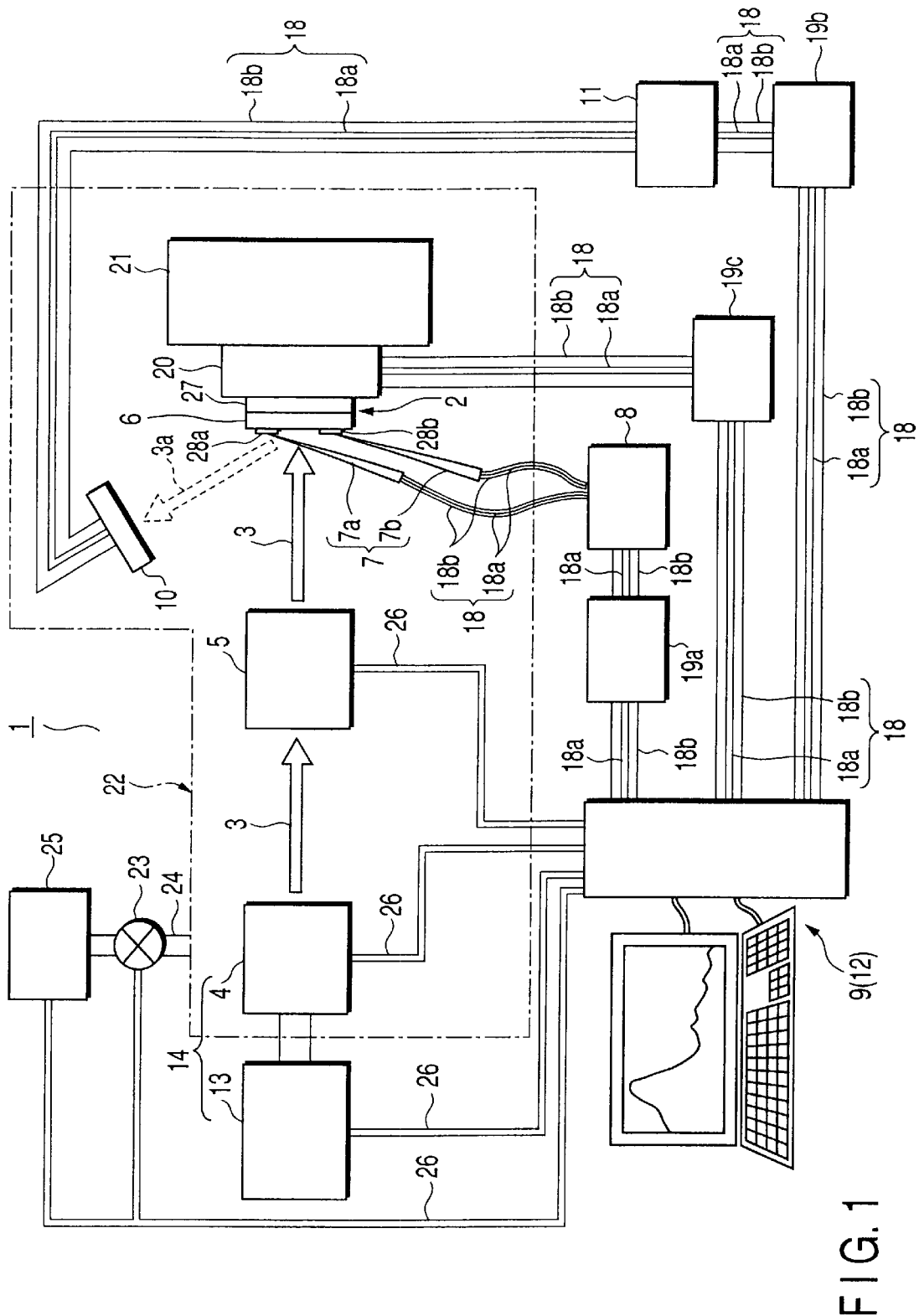
F I G. 1

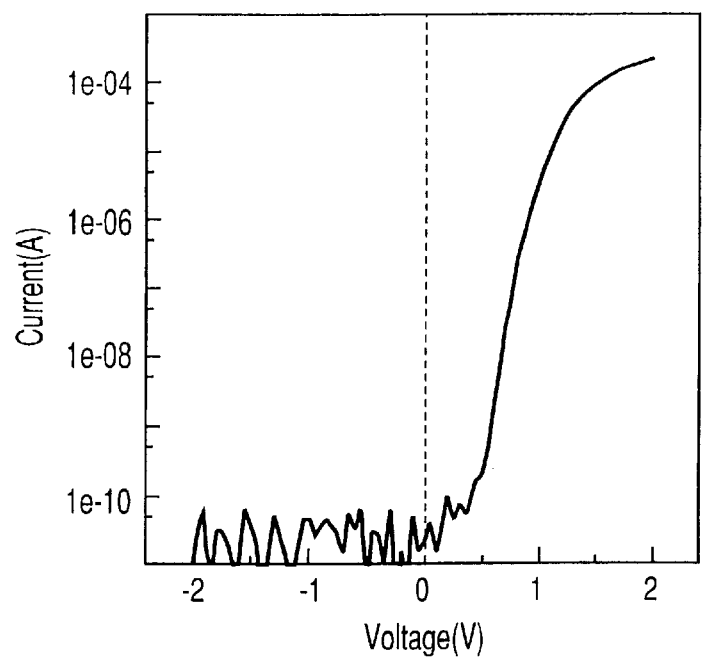
F I G. 7
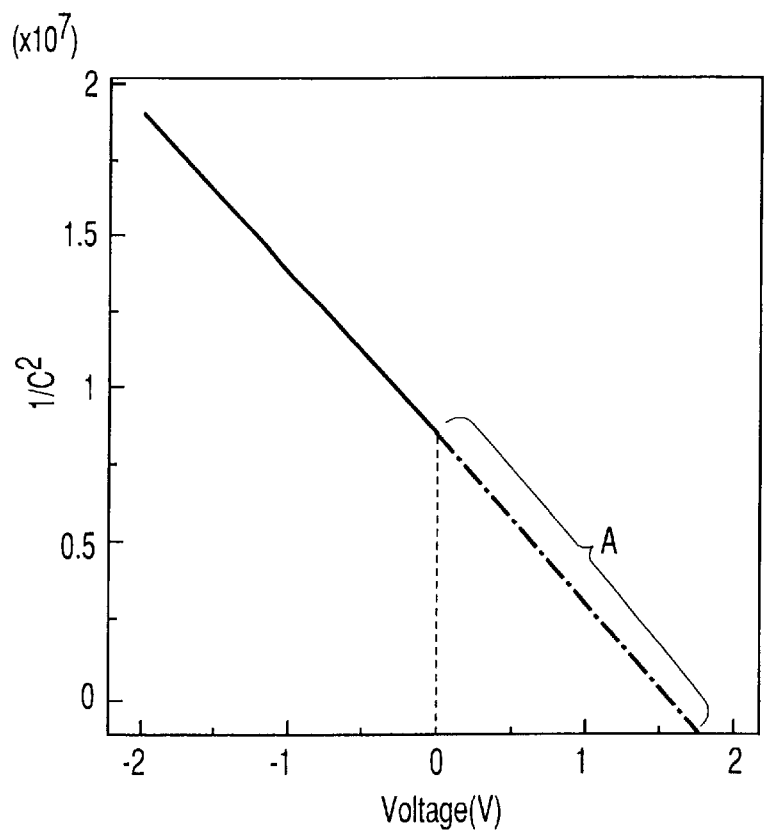
F I G. 8

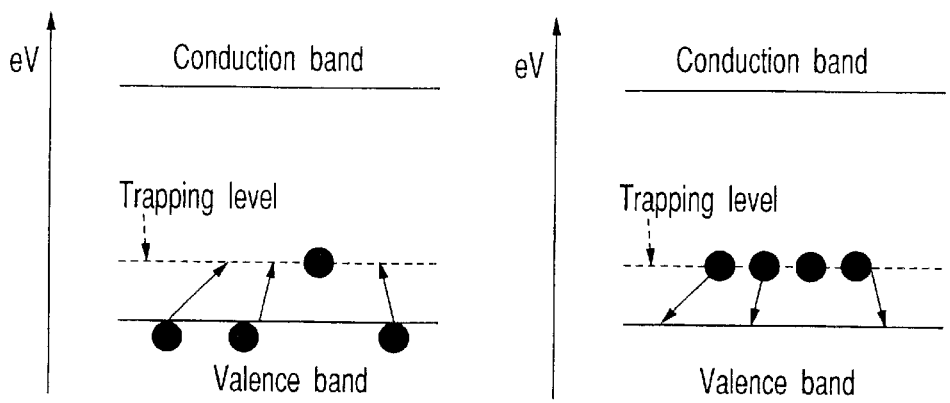
FIG. 14 (PRIOR ART)
FIG. 15 (PRIOR ART)
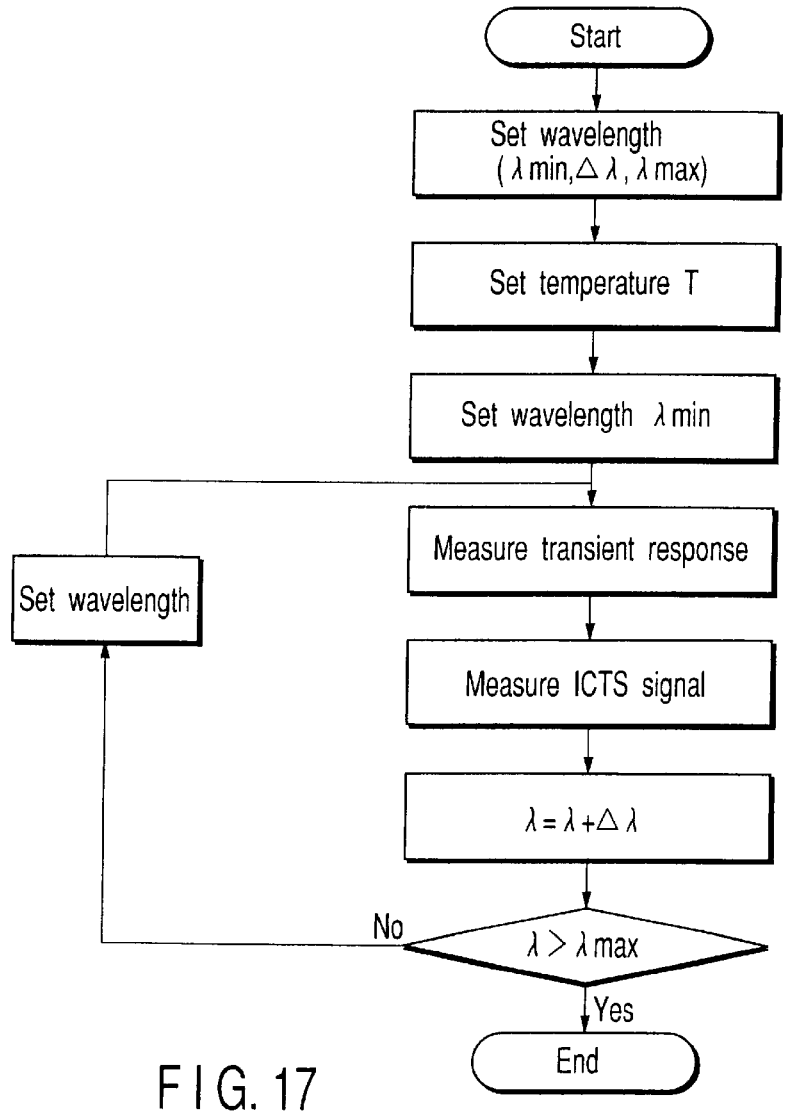
FIG. 17

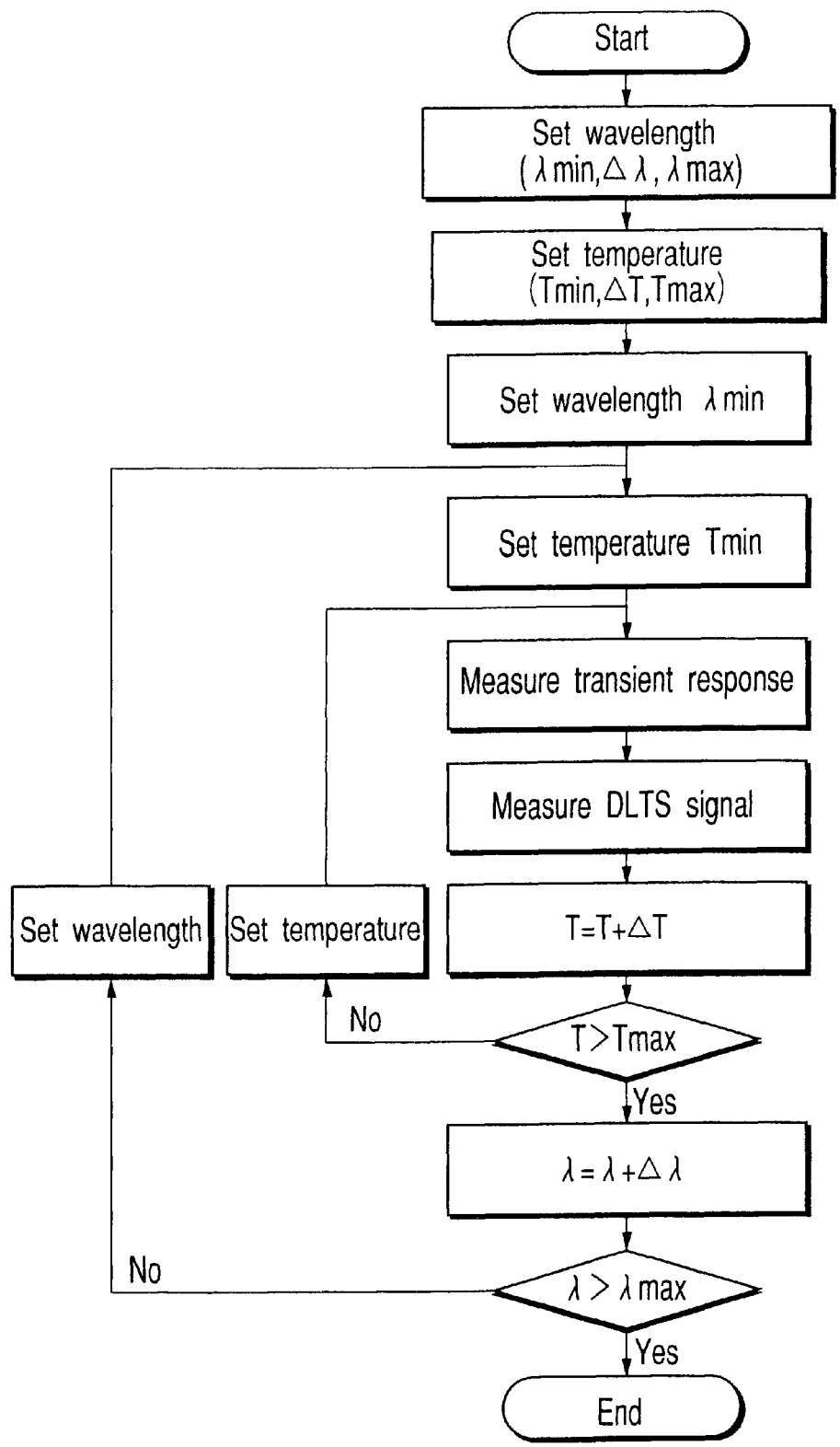
F I G. 16

EVALUATION METHOD AND EVALUATION APPARATUS FOR SEMICONDUCTOR DEVICE

CROSS-REFERENCE TO RELATED APPLICATIONS

This application is based upon and claims the benefit of priority from the prior Japanese Patent Application No. 2001-078517, filed Mar. 19, 2001, the entire contents of which are incorporated herein by reference.

BACKGROUND OF THE INVENTION

1. Field of the Invention

The present invention relates to a method and an apparatus for measuring, analyzing and evaluating the correlation between electrical properties and structural characteristics of a semiconductor device by using an X-ray beam.

2. Description of the Related Art

As a method for evaluating electrical properties of a semiconductor device, there is known a so-called DLTS (Deep Level Transient Spectroscopy) method or an ICTS (Isothermal Capacitance Transient Spectroscopy) method. Electrical properties of impurities or defects in the semiconductor can be obtained by using the DLTS method or the ICTS method. However, information concerning an internal structure of the semiconductor or electron states of a conduction band in a vicinity of a defect in the semiconductor can not be acquired. Further, it is impossible to select a specific type of atom or element from multiple kinds and a plurality of atoms or elements in a semiconductor, and to excite the inner shell of the specific type of atom or element in order to obtain information thereof. Therefore, it is almost impossible to clarify the correlation between the fine structures of impurities, defects, or the vicinity of them in the semiconductor and their electrical properties by using the DLTS method or the ICTS method.

As means for observing the fine structure or electron states at the atomic scale of a sample by using electrical means, there is, for example to be measured, a scanning tunneling microscope (STM). However, although STM can observe the structure or electron states of a surface layer portion of the sample, it can hardly observe the inside of the sample. Furthermore, the sample that STM can observe is restricted to a conductive sample base d on the measurement principle of STM. In case of using STM to observe an insulator, the surface of the insulator must be coated with a conductive material, and the original surface structure of the insulator is deteriorated. Thus, STM can hardly finely observe at the atomic scale the structure or electron states of an insulating film provided in the semiconductor device.

Moreover, as a method for finely and accurately analyzes the internal structure or electron states of the sample at the atomic scale without using electrical means, there is known, for example, an X-ray absorption fine structure (XAFS) method that analyzes the structure by using X-rays. This XAFS method is one type of the absorption spectrum method, and roughly divided into two types, i.e., an X-ray absorption near-edge structure (XANES) method and an extended X-ray absorption fine structure (EXAFS) method. A combined use of the XANES method and the EXAFS method can finely analyze the structure or electron states of various materials contained in a sample, at the atomic scale. The XANES method or the EXAFS method is, however, exclusively used for analysis of the fine structure of a sample to be measured and rarely used for analysis of electrical properties of a sample.

Therefore, the highly reliable evaluation method or evaluation apparatus that can measure and analyze structural characteristics and electrical properties of the semiconductor by associating them with each other, and clarify the relationship between structural characteristics and electrical properties is not substantially established.

BRIEF SUMMARY OF THE INVENTION

It is an object of the present invention to provide an evaluation method and an evaluation apparatus for a semiconductor device which can accurately measure, analyze and evaluate electrical properties, structural characteristics and electron states of a semiconductor device by using an X-ray beam, and can clarify the correlation between electrical properties, structural characteristics and electron states of a semiconductor device with the high reliability, irrespective of a part of the semiconductor device to be measured or a material to be measured.

According to one aspect of the present invention, there is provided a method for evaluating a semiconductor device, comprising the steps of: evaluating electrical properties of a semiconductor device by measuring and analyzing a junction capacitance of a semiconductor provided in the semiconductor device and a transient change of the junction capacitance while applying an X-ray beam to the semiconductor device intermittently; and evaluating a structure and electron states of the semiconductor by measuring and analyzing an energy spectrum of an X-ray beam absorbed into an element present in the semiconductor while applying an X-ray beam to the semiconductor device continuously.

According to the present invention, electrical properties, a structure and electron states of a semiconductor provided in a semiconductor device can be measured, analyzed and evaluated by using an X-ray beam that is being set an appropriate application mode of it to the semiconductor device, in accordance with an evaluating purpose for the semiconductor device. Therefore, electrical properties, structural characteristics and electron states of the semiconductor device can be analyzed and evaluated with the high accuracy, and the relationship between them can be clarified with the high reliability.

According to one aspect of the present invention, there is provided an apparatus for evaluating a semiconductor device, comprising: an X-ray beam applying device which applies an X-ray beam to a semiconductor device; an X-ray beam application-time setting device which switches a mode of applying the X-ray beam to the semiconductor device, between an intermittent application mode and a continuous application mode, and which sets an X-ray beam application-time to prescribed values; a junction capacitance detecting device which detects a junction capacitance of a semiconductor provided in the semiconductor device and a transient change of the junction capacitance while the X-ray beam is being intermittently applied to the semiconductor device; a junction capacitance measurement device which measures the junction capacitance and the transient change thereof, both detected by the junction capacitance detecting device; a first evaluation device which analyzes the junction capacitance and the transient change thereof, both measured by the junction capacitance measurement device and which evaluates electrical properties of the semiconductor device; an X-ray spectrum detecting device which detects an energy spectrum of the X-ray beam continuously applied to and absorbed into an element present in the semiconductor, while the X-ray beam is being continuously applied to the semiconductor device; an X-ray spectrum measurement device which measures the energy spectrum detected by the X-ray beam spectrum detecting device; and a second evaluation device which analyzes the energy spectrum measured by the X-ray beam spectrum measurement device and which evaluates a structure and electron states of the semiconductor device.

According to the present invention, electrical properties, a structure and electron states of a semiconductor provided in a semiconductor device can be measured, analyzed and evaluated by using an X-ray beam that is being set an appropriate application mode of it to the semiconductor device, in accordance with an evaluating purpose for the semiconductor device. In addition, such setting of the appropriate application mode of the X-ray beam, and measurement, analysis and evaluation by using the X-ray beam can be carried out by one apparatus. Therefore, electrical properties, structural characteristics and electron states of the semiconductor device can be analyzed and evaluated with the high accuracy, and the relationship between them can be clarified with the high reliability.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and comprise a part of the specification, illustrate presently aspects of the invention, and together with the general description given above and the detailed description of the aspects given below, serve to explain the principles of the invention.

FIG. 1 is a view showing a schematic structure of an evaluation apparatus for a semiconductor device according to an aspect according to the present invention;

FIG. 7 is a view showing the electric current/voltage characteristic of the diode in the form of a graph;

FIG. 8 is a view showing $1/C^2$ with respect to the voltage of the diode in the form of a graph;

FIG. 14 is a view typically showing the state of a carrier at a rising part of the graph illustrated in FIG. 13;

FIG. 15 is a view typically showing the state of a carrier at an attenuating part of the graph of FIG. 13;

FIG. 16 is a view showing a flow of the SR-DLTS method executed by an evaluation method for a semiconductor device according to an aspect of the present invention in the form of a flowchart;

FIG. 17 is a view showing a flow of the SR-ICTS method executed by an evaluation method for a semiconductor device according an aspect of the present invention in the form of a flowchart;

DETAILED DESCRIPTION OF THE INVENTION

Figure 2:
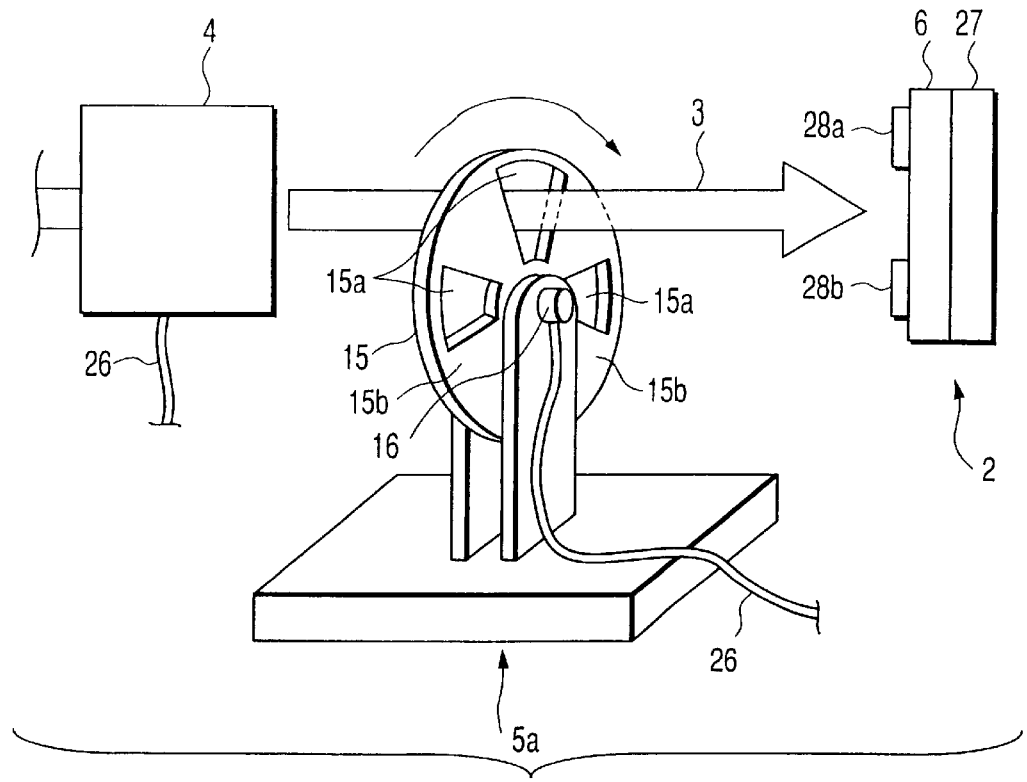
FIG. 2 is a perspective view showing a diode is being applied an X-ray beam.

A method and an apparatus for evaluating a semiconductor device according to one aspect of the present invention will now be described with reference to FIGS. 1 to 24.

An apparatus for evaluating a semiconductor device 1 according to this aspect will be first explained. In the following description, the apparatus for evaluating a semiconductor 1 will be simply referred to as an evaluation apparatus 1.

As shown in FIG. 1, an X-ray beam applying device 4 provided in the evaluation apparatus 1 is integrally configured with an X-ray beam generating device 13 as an X-ray beam source which generates an X-ray beam 3 which is applied to a semiconductor device 2 as a sample. A wavelength, energy, diameter, and other properties of the X-ray beam 3 can be independently set by the X-ray beam applying device 4 and the X-ray beam generating device 13. It is preferable that the X-ray beam applying device 4 and the X-ray beam generating device 13 comprise, for example, a synchrotron 14 as an X-ray beam applying device which can generate synchrotron (orbital) radiation (SOR, SR) light and apply it as the continuous X-ray beam 3 having the large intensity. In particular, it is preferable that a non-illustrated beam line for XAFS measurement is provided to the X-ray beam applying device 4. As such a synchrotron 14, specifically, a Photon Factory Ring BL12C or a Spring 8 that is set in Japan is suitable.

The X-ray beam applying device 4 and the X-ray beam generating device 13 are connected to a first evaluation device 9 which evaluates electrical properties of the semi-conductor device 2 and a second evaluation device 12 which evaluates a structure and electron states of the semiconductor device 2 through a connection cable 26, respectively. The operation mode of the synchrotron 14 is controlled by the first evaluation device 9 and the second evaluation device 12 so that the synchrotron 14 can generate the continuous X-ray beam 3 with which the both devices 9 and 12 can appropriately and accurately evaluate the semiconductor device 2 and it can apply the continuous X-ray beam 3 toward the semiconductor device 2.

As shown in FIG. 1 the X-ray beam application-time setting device 5 is arranged on a traveling path of the X-ray beam 3 applied toward the semiconductor device 2 from the X-ray beam applying device 4 between the X-ray beam applying device 4 and the semiconductor device 2. The X-ray beam application-time setting device 5 is connected to the first evaluation device 9 and the second evaluation device 12 through the connection cable 26. The operation mode of the X-ray beam application-time setting device 5 is controlled by the first evaluation device 9 and the second evaluation device 12 so that the X-ray beam 3 with which the both devices 9 and 12 can appropriately and accurately evaluate the semiconductor device 2 can be applied to the semiconductor device 2.

It is preferable that the X-ray beam application-time setting device 5 is controlled in such a manner that selective changeover of intermittent application or continuous application of the X-ray beam 3 with respect to the semiconductor device 2 is appropriately synchronized with a proper timing in accordance with an evaluation purpose for the semiconductor device 2. Specifically, in case of evaluating electrical properties of the semiconductor device 2 by detecting and measuring the junction capacitance and its transient change of a semiconductor 6 provided in the semiconductor device 2, the X-ray beam application-time setting device 5 is controlled in such a manner that the intermittent X-ray beam 3 is applied from the synchrotron 14 toward the semiconductor device 2. At this moment, identification, concentration and level energy of impurities in the semiconductor 6, a depth and density of a trapping level, a trapping cross section and others are measured and analyzed. Alternatively, in case of evaluating the structure and electron states of the semiconductor device 2 by detecting and measuring an energy spectrum of the continuous X-ray beam 3 absorbed in an element present in the semiconductor 6, the X-ray beam application-time setting device 5 is controlled in such a manner that the continuous X-ray beam 3 is applied from the synchrotron 14 toward the semiconductor device 2. At this moment, impurities or defects in the semiconductor 6, the local structure (fine structure) around them at the atomic scale, or the like are measured and analyzed.

Figure 3:
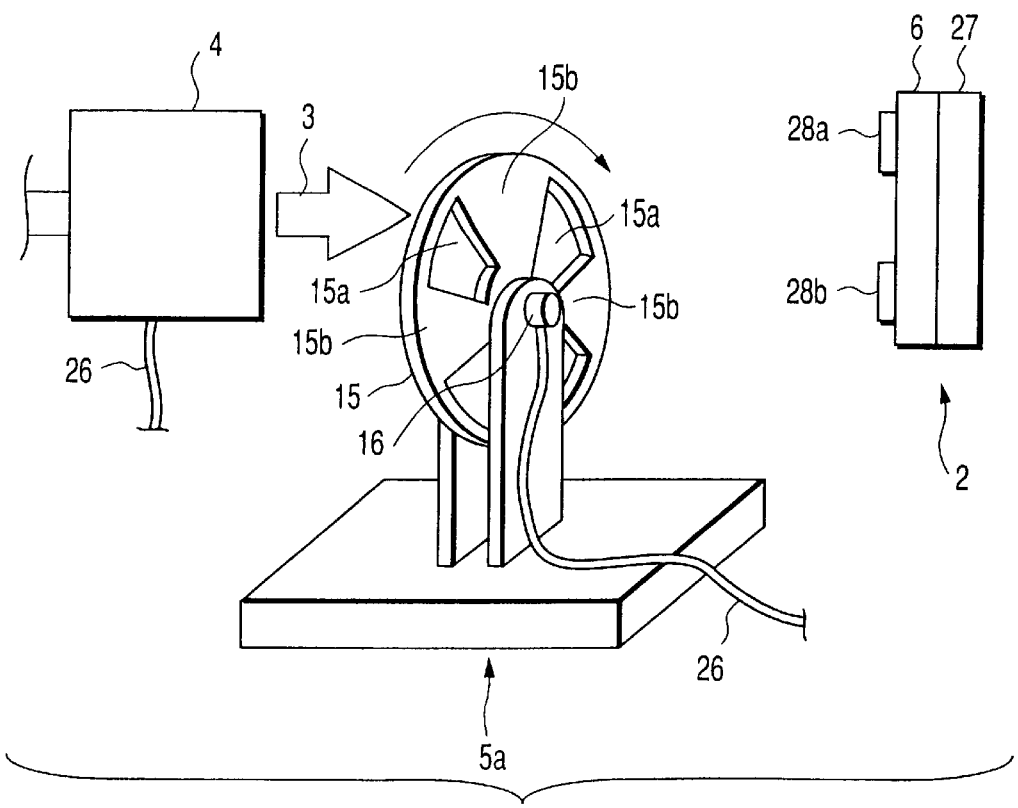
FIG. 3 is a perspective view showing an X-ray beam intercepted by an X-ray beam chopper.

In this aspect, as the X-ray beam application-time setting device 5, there is used an X-ray beam chopper 5a formed of a material capable of intercepting the X-ray beam 3 as shown in FIGS. 2 and 3. The X-ray beam chopper 5a will now be described hereinafter in detail with reference to FIGS. 2 and 3.

The X-ray beam chopper 5a provides a rotor plate 15 to which a plurality of X-ray beam passing holes 15a for passing the X-ray beam 3 therethrough are provided, a drive motor 16 for driving the rotor plate 15 to rotate, and others. Each X-ray beam passing hole 15a is formed into a prescribed size and shape so that the X-ray beam 3 whose quantity is sufficient for the first evaluation device 9 and the second evaluation device 12 to appropriately and accurately evaluate the semi-conductor device 2 can pass therethrough and it can be applied to the semiconductor device 2. The respective X-ray beam passing holes 15a are provided so as to be distanced from each other at equal intervals along the circumferential direction of the rotor plate 15. The space between the respective X-ray beam passing holes 15a is formed as an X-ray beam interception portion 15b through which the X-ray beam 3 can not pass. The X-ray beam chopper 5a is arranged so that the rotor plate 15 can be positioned on the traveling path of the X-ray beam 3 indicated by outline arrows in FIGS. 2 and 3, for example.

In cases where the semiconductor device 2 is being applied the pulse-like intermittent X-ray beam 3, for example, the drive motor 16 is operated at a prescribed rotational speed so that the rotor plate 15 is rotated at an equal speed in a direction indicated by solid arrows in FIGS. 2 and 3. Then, as shown in FIG. 2, the applied mode that the X-ray beam 3 can pass through each X-ray beam passing hole 15a and reach the semiconductor device 2, as shown in FIG. 3 and the non-applied mode that the X-ray beam 3 is intercepted by each X-ray beam interception portion 15b and can not reach the semiconductor device 2 are alternately repeated with a fixed cycle. As a result, the continuous X-ray beam 3 generated by the synchrotron 14 can be processed to the pulse-like intermittent X-ray beam 3, and the semiconductor device 2 can be intermittently applied this X-ray beam 3. The application cycle of the intermittent X-ray beam 3 can be appropriately set to a proper interval by changing the rotational speed of the rotor plate 15 in accordance with components of the semiconductor 6 or the evaluation accuracy.

Additionally, in cases where the semiconductor device 2 is being applied the continuous X-ray beam 3, as shown in FIG. 2, it is good enough that the drive motor 16 is operated so that the X-ray beam passing hole 15a is positioned on the traveling path of the X-ray beam 3, the operation is then stopped and the position of the rotor plate 15 is maintained. As a result, the semiconductor device 2 can be continuously applied the continuous X-ray beam 3 generated by the synchrotron 14. The application time of the continuous X-ray beam 3 can be appropriately set to a proper length by changing the stop time of the rotor plate 15 in accordance with components of the semiconductor 6, the evaluation accuracy or the like.

Figure 4:
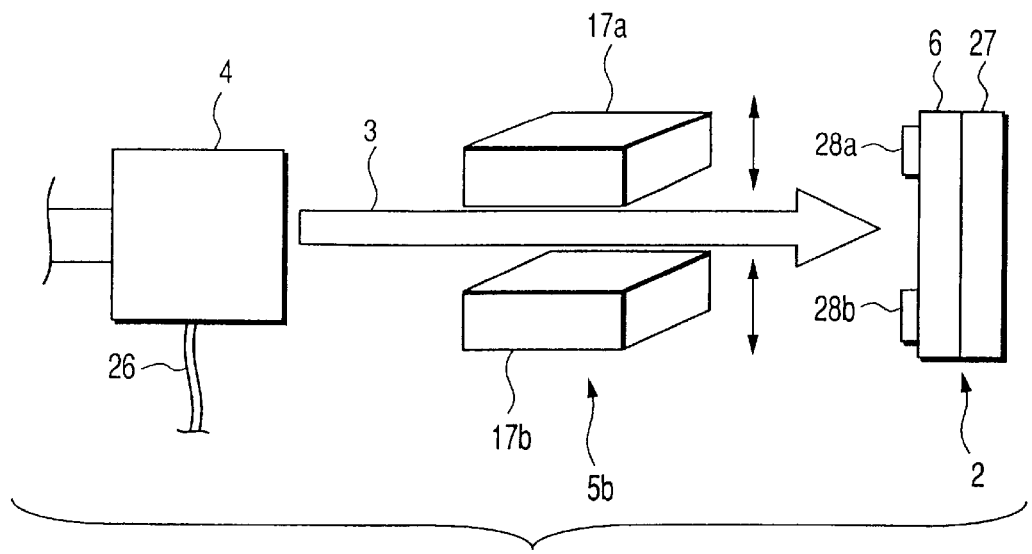
FIG. 4 is a perspective view showing a diode is being applied an X-ray beam.
Figure 5:
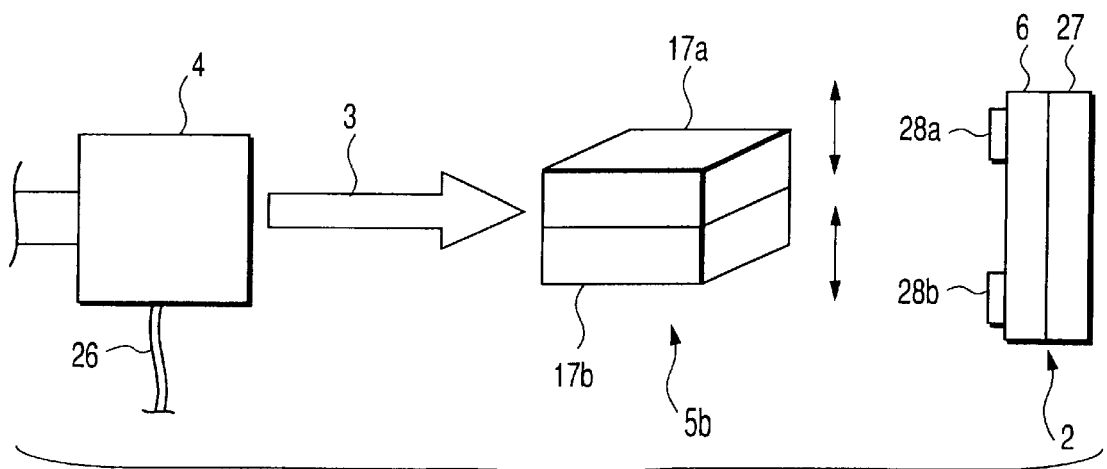
FIG. 5 is a perspective view showing an X-ray beam intercepted by a gate valve.

Further, the X-ray beam application-time setting device 5 is not restricted to the above-described X-ray beam chopper 5a. For example, as shown in FIGS. 4 and 5, it is possible to use a gate valve 5b comprised by a pair of a first valve body 17a and a second valve body 17b or the like formed of a material capable of intercepting the X-ray beam 3. The gate valve 5b is arranged on the traveling path of the X-ray beam 3 indicated by outline arrows in FIGS. 4 and 5 as similar to the X-ray beam chopper 5a mentioned above. The first valve body 17a and the second valve body 17b are set so as to be capable of moving in directions along which they are separated from each other by a non-illustrated drive device as indicated by solid arrows in FIGS. 4 and 5, for example. The operation mode of the gate valve 5b is likewise controlled by the first evaluation device 9 and the second evaluation device 12, as similar to the above-described X-ray beam chopper 5a.

In cases where the semiconductor device 2 is being applied the X-ray beam 3, as shown in FIG. 4, the distance between the first valve body 17a and the second valve body 17b is opened so that the X-ray beam 3 can pass therethrough, and the gate valve 5b is set to a so-called opened mode. Consequently, the X-ray beam 3 applied from the X-ray beam applying device 4 toward the semiconductor device 2 can pass between the first valve body 17a and the second valve body 17b and reach the semiconductor device 2. Furthermore, in cases where the semiconductor device 2 is not applied the X-ray beam 3, as shown in FIG. 5, the both valve bodies 17a and 17b are appressed against each other so that the X-ray beam 3 can not pass between the first valve body 17a and the second valve body 17b, and the gate valve 5b is set to a so-called closed mode. As a result, the X-ray beam 3 applied from the X-ray beam applying device 4 toward the semiconductor device 2 can not reach the semiconductor device 2 since its traveling path is intercepted by the gate valve 5b.

In case of evaluating electrical properties of the semiconductor device 2, the opened mode or the closed mode of the gate valve 5b is alternately repeated with a fixed cycle, respectively. Consequently, the semiconductor device 2 can be applied the pulse-like intermitted X-ray beam 3. The application cycle of the intermittent X-ray beam 3 can be appropriately set to a proper interval by changing the cycle of opening/closing of the gate valve 5b in accordance with, e.g., components of the semiconductor 6 provided in the semiconductor device 2. Furthermore, in case of evaluating the fine structure and electron states of the semiconductor device 2, setting the gate valve 5b to the opened mode and maintaining that mode for a prescribed time can suffice. As a result, the semiconductor device 2 can be applied the continuous X-ray beam 3. The application time of the continuous X-ray beam 3 can be appropriately set to a proper length by changing the opening time of the gate valve 5b in accordance with, e.g., components of the semiconductor 6 provided in the semiconductor device 2.

As described above, even if the gate valve 5b is used, the continuous application mode or the intermittent application mode of the X-ray beam 3 can be appropriately selectively switched in accordance with an evaluation purpose of the semiconductor device 2, or the application-time of the X-ray beam 3 can be appropriately set to a proper length.

Further, when performing each evaluation mentioned above, for example, a non-illustrated sensor may be set to detect whether the operating mode of the X-ray beam application-time setting device 5 is appropriate or not. In such a case, it is good enough that a part or all of the evaluation apparatus 1 is set so as to be safely and rapidly stopped when the sensor detects that the operating mode of the X-ray beam application-time setting device 5 enters the inappropriate mode.

For example, in case of evaluating electrical properties of the semiconductor device 2, when the rotor plate 15 of the X-ray beam chopper 5a becomes stationary or the gate valve 5b remains the opened mode or the closed mode, the sensor detects it as an inappropriate mode and outputs this detected information as an electric signal to the first evaluation device 9. Upon receiving the signal from the sensor, the first evaluation device 9 outputs a command to stop applying of the continuous X-ray beam 3 to the X-ray beam applying device 4 through the connection cable 26 as an electric signal. As a result, the possibility that electrical properties of the semiconductor device 2 are evaluated in the inappropriate mode can be almost avoided.

Similarly, in case of evaluating the fine structure or electron states of the semiconductor device 2, when the rotor plate 15 of the X-ray beam chopper 5a remains the rotating mode or the gate valve 5b repeats the opened mode and the closed mode, the sensor detects it as an inappropriate mode and outputs the detected information as an electric signal to the second evaluation device 12. Upon receiving the signal from the sensor, the second evaluation device 12 outputs a command to stop applying of the continuous X-ray beam 3 to the X-ray beam applying device 4 through the connection cable 26 as an electric signal. As a result, the possibility that the fine structure or electron states of the semiconductor device 2 are evaluated in the inappropriate mode can be almost avoided.

Furthermore, with such a setting, failures due to an erroneous operation of the evaluation apparatus 1 which is a precision instrument can be almost avoided and the duration of life of the evaluation apparatus 1 can be prolonged.

As shown in FIG. 1, a probe 7 provides a pair of a first needle 7a and a second needle 7b or the like is used as the junction capacitance detecting device which detects a junction capacitance and its transient change of the semiconductor 6 provided in the semiconductor device 2. Both the first needle 7a and the second needle 7b are formed of a prescribed pure metal suitable for detecting the junction capacitance or the like of the semiconductor 6. As shown in FIG. 1, each of the first needle 7a and the second needle 7b is connected to the later-described junction capacitance measurement device 8 through a shielded cable 18 as a noise reduction device.

The shielded cable 18 is comprised by, e.g., a core wire 18a and a shielded wire 18b which is provided so as to cover the core wire 18a from the outside thereof. The core wire 18a is formed of a metal having the low resistivity such as copper or gold. Moreover, the shielded wire 18b is formed of a material that can protect the core wire 18a from a so-called noise such as electromagnetic waves, heat and light from the outside. As a result, the junction capacitance and its transient change of the semiconductor 6 detected by the probe 7 are hardly interfered with the noise even if the installation space of the evaluation apparatus 1 is very small, for example. Therefore, the junction capacitance and its transient change are outputted to the junction capacitance measurement device 8 without being deteriorated as an analog electric signal.

As the junction capacitance measurement device 8 which measures the junction capacitance and its transient change of the semiconductor 6, a device capable of measuring the junction capacitance C and its transient change (transient capacitance C) detected by the probe 7 or an electric current (transient current response I) which flows through a non-illustrated junction of the semiconductor 6 is suitable. In this aspect, an IV/CV meter 8 is used as the junction capacitance measurement device. The IV/CV meter 8 is connected through the shielded cable 18 to a first A/D converter 19a that converts an analog signal transmitted from the probe 7 into a digital signal in order to facilitate evaluation by the first evaluation device 9. Consequently, the analog signal measured by the IV/CV meter 8 is converted into a digital signal without being deteriorated by the first A/D converter 19a.

A device capable of appropriately and accurately analyzing the electric signal from the probe 7, which has been converted into a digital signal by the first A/D converter 19a, and easily performing evaluation is suitable as the first evaluation device 9 which evaluates electrical properties of the semiconductor device 2. In this aspect, a first computer 9 such as a workstation or a personal computer that provides prescribed analysis software (evaluation software) is used as the first evaluation device. This evaluation software evaluates electrical properties of the semiconductor device 2 by analyzing the electric signal which has been detected as an analog signal by the probe 7, outputted to the IV/CV meter 8 and converted into a digital signal by the first A/D converter 19a. The first computer 9 is connected to the first A/D converter 19a through the shielded cable 18.

With such a setting, the system which is comprised by the probe 7, the IV/CV meter 8, the first A/D converter 19a and the first computer 9 or the like and evaluates electrical properties of the semiconductor device 2 can appropriately and accurately detect, measure, analyze and evaluate electrical properties of the semiconductor device 2.

As shown in FIG. 1, a so-called X-ray detector 10 is used as the X-ray spectrum detecting device that detects an energy spectrum of the continuous X-ray beam 3 absorbed in an element present in the semiconductor 6 provided in the semiconductor device 2. This X-ray detector 10 is movably arranged so as to be capable of detecting a so-called reflected (scattered) X-ray beam 3a derived from reflection or scattering of the X-ray beam 3 applied from the X-ray beam applying device 4 toward the semiconductor device 2 as indicated by the outline arrow in FIG. 1 by the semiconductor device 2 as indicated by a broken arrow in FIG. 1. The X-ray detector 10 indirectly detects an energy spectrum of the continuous X-ray beam 3 absorbed in an element present in the semiconductor 6 by directly detecting an energy spectrum of the reflected X-ray beam 3a. The energy spectrum of the reflected X-ray beam 3a detected by the X-ray detector 10 is outputted to the X-ray spectrum measurement device 11 as an analog electric signal.

The X-ray spectrum measurement device 11 which measures the energy spectrum of the reflected X-ray beam 3a detected by the X-ray detector 10 is connected the X-ray detector 10 through the shielded cable 18. In addition, the X-ray spectrum measurement device 11 is connected through the shielded cable 18 to a second A/D converter 19b which converts the analog signal transmitted from the X-ray detector 10 into a digital signal in order to facilitate evaluation by the second evaluation device 12. The X-ray detector 10, the X-ray spectrum measurement device 11 and the second A/D converter 19b comprise a part of a so-called goniometer.

A device capable of appropriately and accurately analyzing an electric signal from the X-ray detector 10, which has been converted into a digital signal by the second A/D converter 19b, and easily performing evaluation is suitable as the second evaluation device 12 which evaluates the fine structure and electron states of the semiconductor device 2. In this aspect, as the second evaluation device, there is used a second computer 12 such as a workstation or a personal computer which provides prescribed analysis software (evaluation software) or the like, as similar to the first evaluation device 9 mentioned above. This analysis software evaluates the fine structure and electron states or the like of the semiconductor device 2 by analyzing the electric signal that has been detected as an analog signal and outputted to the X-ray spectrum measurement device 11 by the X-ray detector 10 and converted into a digital signal by the second A/D converter 19b. The second computer 12 is connected to the second A/D converter 19b through the shielded cable 18.

With such a setting, the system which is comprised by the X-ray detector 10, the X-ray spectrum measurement device 11, the second A/D converter 19b, the second computer 12 or the like and evaluates the fine structure and electron states or the like of the semiconductor device 2 can appropriately and accurately detect, measure, analyze and evaluate the fine structure and electron states or the like of the semiconductor device 2.

Additionally, in this aspect, a software that evaluates electrical properties of the semiconductor device 2 and a software that evaluates the fine structure and electron states or the like of the semiconductor device 2 are installed in one computer. As a result, the first computer 9 and the second computer 12 can be integrated, and minimization and facility saving of the evaluation apparatus 1 can be thereby achieved. Further, since simultaneously activating two types of such software can evaluate electrical properties of the semiconductor device 2, the fine structure and electron states or the like of the semiconductor device 2 by using one computer at the same time, operations can be reduced and the operating time can be shortened. In the following description, both the first computer 9 and the second computer 12 will be simply referred to as a computer 9 (12).

The evaluation apparatus 1, as shown in FIG. 1, provides a temperature adjustment device 20 capable of setting a temperature of the semiconductor device 2 to prescribed values. Although not shown, the temperature adjustment device 20 provides a Peltier element that can readily switch and perform heating or cooling by changing a direction or a quantity of flow of an electric current. Furthermore, although not shown, the temperature adjustment device 20 has a thermocouple so that a temperature of the semiconductor device 2 can be accurately measured. The Peltier element and the thermocouple are collectively connected to a third A/D converter 19c as the entire temperature adjustment device 20 through the shielded cable 18.

The third A/D converter 19c converts into a digital signal an electric signal concerning a direction or a quantity of flow of the electric current flowing through the Peltier element, a temperature of the Peltier element or a temperature of the semi-conductor device 2 detected by the thermocouple, the electric signal being transmitted as an analog signal from the Peltier element or the thermocouple. As a result, control of the temperature adjustment device 20 can be facilitated. The third A/D converter 19c is connected to the computer 9 (12) through the shielded cable 18. In this aspect, the computer 9 (12) is set to also function as the temperature setting device that controls the temperature adjustment device 20.

With such a setting, since a temperature of the semiconductor device 2 at the time of evaluating the semiconductor device 2 can be appropriately and accurately detected, measured and set, the evaluation accuracy of the semiconductor device 2 by the evaluation apparatus 1 can be improved.

Furthermore, as shown in FIG. 1, the evaluation apparatus 1 provides a vibration removing base 21 as a noise reduction device capable of holding so as not to conduct vibrations to the semiconductor device 2 attached to the temperature adjustment device 20. As a result, the position of the semiconductor device 2 at the time of evaluating the semiconductor device 2 can be stabilized, and the evaluation accuracy of the semiconductor device 2 by the evaluation apparatus 1 can be hence improved.

As indicated by a part surrounded by a chain line in FIG. 1, the evaluation apparatus 1 is configured to be capable of setting a measurement environment 22 including at least the X-ray beam applying device 4, the X-ray beam application-time setting device 5, the probe 7, the X-ray detector 10, the temperature adjustment device 20, the vibration removing base 21, the semiconductor device 2 or the like in the X-ray optical system to a prescribed pressure state. For example, it is assumed that the measurement environment 22 is accommodated in a non-illustrated chamber having the high airtightness holding property. To the chamber is connected a vacuum pump 25 as a pressure adjustment device through an opening/closing valve 23 and an air pipe 24. The opening/closing valve 23 and the vacuum pump 25 are connected to the computer 9 (12) through a connection cable 26. Controlling the opened/closed mode of the opening/closing valve 23 and the operating mode of the vacuum pump 25 by the computer 9 (12) can set the pressure in the chamber to a desired level.

Specifically, in case of reducing below the ambient pressure the pressure in the measurement environment 22 set to the pressure which is substantially equal to, e.g., the ambient pressure, the vacuum pump 25 is operated while maintaining the opening/closing valve 23 closed, and the gas in the chamber is emitted to the outside of the chamber through the air pipe 24. As a result, the pressure in the chamber is lowered. By stopping the operation of the vacuum pump 25 while keeping the opening/closing valve 23 closed after the pressure in the chamber has reached a desired value, the pressure in the measurement environment 22 can be held lower than the ambient pressure. Alternatively, as described above, in case of returning the pressure in the measurement environment 22 held lower than the ambient temperature to the pressure that is substantially equal to the ambient temperature, the closed opening/closing valve 23 is opened while maintaining stop of the operation of the vacuum pump 25. As a result, the gas outside the chamber flows into the chamber through the air pipe 24. When the pressure in the chamber, namely, the pressure in the measurement environment 22 becomes equal to the ambient pressure, flow of the air into the chamber naturally stops.

If a small amount of gas exists in the measurement environment 22 when the energy of the X-ray beam 3 applied to the semiconductor device 2 is, e.g., approximately 1000 eV, the X-ray beam 3 is absorbed or scattered by the gas. Consequently, most of the energy of the X-ray beam 3 required for evaluating the semiconductor device 2 is attenuated and lost before the X-ray beam 3 reaches the semiconductor device 2. Therefore, in case of evaluating the semiconductor device 2 by using the X-ray beam 3 having the low energy, the inside of the measurement environment 22 must be generally set to the high vacuum state. According to the evaluation apparatus 1 of this aspect, since the intensity of the pressure in the measurement environment 22 can be set to a desired high vacuum state in accordance with the intensity of the energy of the X-ray beam 3, the turbulence of the X-ray beam 3 can be suppressed. Moreover, since the evaluation apparatus 1 can emit the gas in the measurement environment 22 to the outside, it can eliminate the possibility that the semiconductor device 2 may be transformed due to the atmosphere in the measurement environment 22, and evaluate the semiconductor device 2 in the stable state.

As described above, according to the evaluation apparatus 1 of the aspect of the present invention, electrical properties, structural characteristics and electron states or the like of the semiconductor device 2 can be accurately and easily measured, analyzed and evaluated in the appropriate mode by using the X-ray beam 3. Thus, the relevance of structural characteristics and electrical properties of the semiconductor device 2 can be revealed with the high reliability.

An evaluation method for a semiconductor device according to an aspect of the present invention will now be described based on the experiment conducted by the present inventors. In the following description, this evaluation method for a semiconductor device will be simply referred to as an evaluation method hereinafter. The evaluation method according to this aspect is carried out by using the above-described evaluation apparatus 1.

Figure 6:
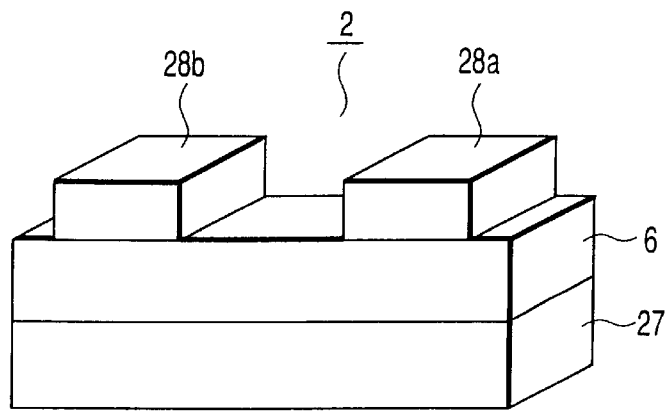
FIG. 6 is a perspective view showing a schematic structure of an Au/n type GaN Schottky diode.

As the semiconductor device 2 as a sample to be measured, there is used a so-called Au/n type GaN Schottky diode 2. FIG. 6 typically shows the schematic structure of this diode 2. The diode 2 is obtained by forming a film of the semiconductor 6 comprising of gallium nitride (GaN) obtained by doping silicon (Si) on a sapphire ($Al_2O_3$) substrate 27 by the MOCVD method. A Schottky electrode 28a as a first electrode made from gold (Au) and an ohmic electrode 28b as a second electrode made from aluminium (Al) are formed on the substrate 27, respectively, by the vacuum deposition method.

Before evaluating electrical properties, the fine structure and electron states of the diode 2, whether the diode 2 can operate in the appropriate mode was examined or not. The first needle 7a of the probe 7 in the evaluation apparatus 1 is brought into contact with the Schottky electrode 28a, and the second needle 7b is brought into contact with the ohmic electrode 28b, respectively. In this state, a voltage of −2 to +2 V is applied to the first needle 7a and the second needle 7b so as to cause the electric currents in the forward and reverse directions to flow to the semiconductor 6 of the diode 2. Showing the result of this examination in a graph as the correlation of the electric current and the voltage, an electric current/voltage characteristic curve such as shown in FIG. 7 was obtained. Based on this electric current/voltage characteristic curve, it can be understood that the diode 2 is an excellent ideal Schottky diode having the small electric current in the reverse direction.

In addition, showing the result of this examination in a graph as the correlation of $1/C^2$ and the voltage, a characteristic curve such as shown in FIG. 8 was obtained. Based on this characteristic curve, it can be understood that the diode 2 is an excellent ideal Schottky diode and has a step junction comprising of the substantially uniform concentration profile. Incidentally, a part A indicated by a chain line in FIG. 8 is obtained by extrapolating the approximated curve so as to be continuous to a part indicated by a solid line in FIG. 8. Based on the result shown in FIG. 8 and others, it can be understood that the impurity density of the sapphire substrate 27 of the diode 2 and the Schottky barrier are $4.57 \times 10^{17}/cm^3$ and 1.60 eV, respectively.

Subsequently, the capacitance (the depletion layer capacitance, the junction capacitance) of the semiconductor 6 of the diode 2 was measured by applying a bias voltage obtained by superimposing an alternating signal of 100 kHz to the Schottky electrode 28a. Simultaneously, the dependency of the capacitance of the semiconductor 6 on the wavelength of the applied radiation light (X-ray beam) was examined. Specifically, changes in the capacitance of the semiconductor 6 and the time dependency were measured and analyzed by varying the wavelength and the energy or the like of the excited X-ray beam in a vicinity of an K absorption edge of the Ga atom in the semiconductor 6. Showing the results in a graph, they were observed as a clear capacitance XAFS signal as indicated by a solid line in FIG. 9.

Figure 9:
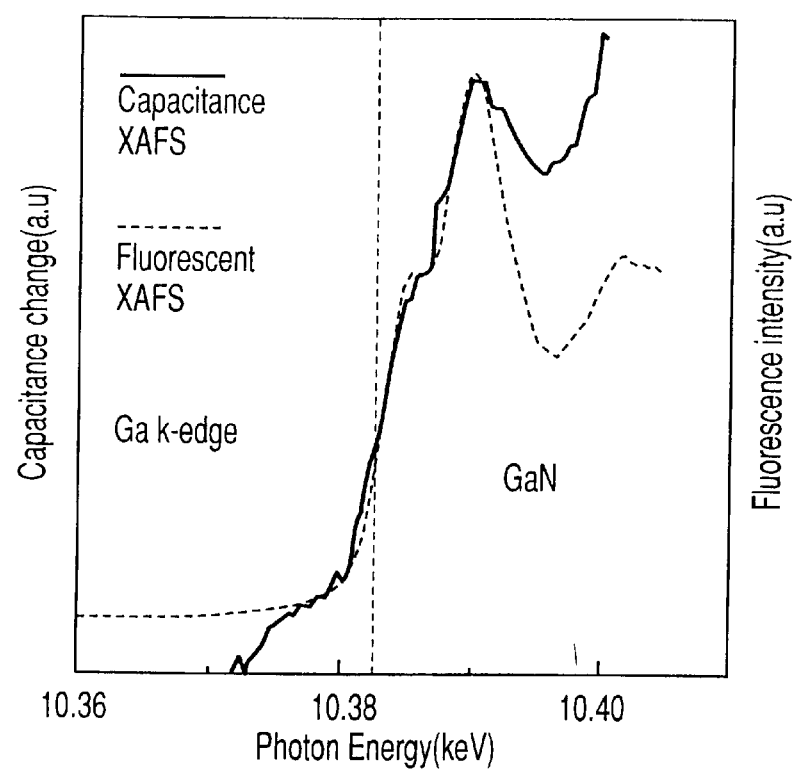
FIG. 9 is a view showing a capacitance XAFS signal and a fluorescent XAFS signal indicative of structural information of the diode in the form of a graph.

Additionally, in order to verify the reliability of the capacitance XAFS signal, the similar measurement and analysis were carried out by using the fluorescent X-ray beam generated by the same excitation source as that of the excited X-ray beam. Showing the result in a graph, a fluorescent XAFS signal such as indicated by a broken line in FIG. 9 was obtained. When the both XAFS signals were compared, it was confirmed that they substantially coincide with each other in the vicinity of the K absorption edge of the Ga atom as shown in FIG. 9. Consequently, it can be understood that information concerning the structure of the diode 2 obtained by the XAFS method according to this aspect has the high accuracy that is reliable as with information obtained by the XAFS method according to the prior art. Further, as a result, since there is no shift in the vicinity of the K absorption edge of the Ga atom, it can be understood that the Ga atom does not relate to defects of the semiconductor 6.

Figure 10:
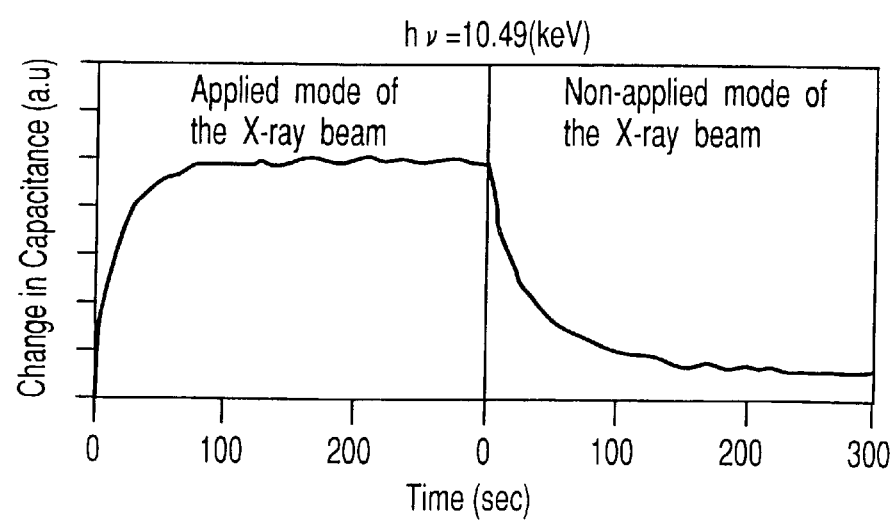
FIG. 10 is a view showing a change with time of a junction capacitance of a semiconductor when the diode is being applied the X-ray beam intermittently at a room temperature in the form of a graph.
Figure 11:
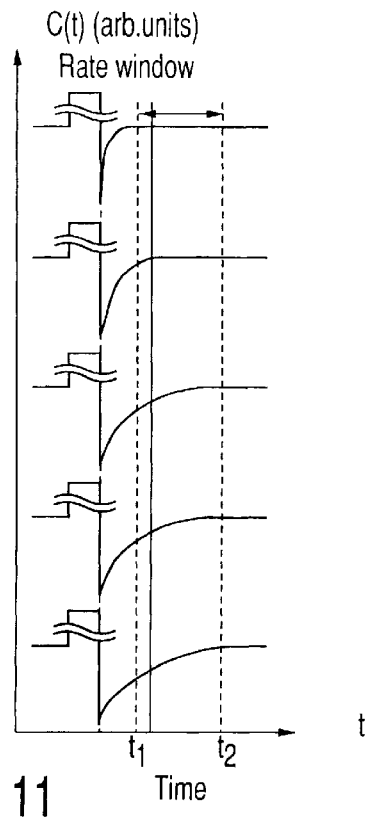
FIG. 11 is a view showing a transient response of a capacitance of a given semiconductor based on the principle of the DLTS method according to the prior art in the form of a graph.

Furthermore, in order to examine the transient reaction (transient response) of the semiconductor 6 with respect to the pulse-like intermittent X-ray beam, the semiconductor 6 was applied the intermittent X-ray beam whose intensity of energy is 10.49 keV at a room temperature, and changes in the capacitance with time were measured. Showing the result in a graph, changes in the transient capacitance having the time constant of the several tens second order were observed as shown in FIG. 10. Such a transient phenomenon of the junction capacitance corresponds to trapping (trap phenomenon) of the carrier (hole) excited at a deep level in the semiconductor 6 from a valence band to a trap level by application of the intermittent X-ray beam, or to emit (de-trap phenomenon) of the same from the trap level to the valence band by thermal excitation. Based on the result of observation, it can be understood that the carrier that the activation energy that the Ga atom in the semiconductor 6 has is at a deep level can be excited by being applied the pulse-like intermittent X-ray beam to the semiconductor 6. Therefore, it can be realized that information concerning electrical properties of the semiconductor device 2 such as identification and concentration of impurities in the semiconductor 6, the level energy, the depth and density of the trapping level, the trapping cross section and others can be obtained by detecting impurities or defects that the activation energy in a forbidden band of the semiconductor 6 has a deep level by using the intermittent X-ray beam.

In this aspect, the continuous X-ray beam used in the XAFS method or the like for obtaining information concerning the structure of a material in the prior art is processed into the pulse-like intermittent X-ray beam by using the X-ray beam chopper 5a or the like, and the diode 2 is applied the obtained X-ray beam. Consequently, the capacitance of the semiconductor 6 that the diode 2 has or a quantity of flow of the electric current flowing through its junction is changed. Then, these values are detected as electric signals, measured and analyzed as a DLTS signal, an ICTS signal or the like used for evaluating electrical properties of the semiconductor 6. As a result, electrical properties of the diode 2 can be evaluated by using the intermittent X-ray beam. Instead of the DLTS method or the ICTS method using electrical exciting means according to the prior art, a method according to this aspect that uses the intermittent X-ray beam and evaluates electrical properties of the diode 2 is referred to as an SR (SOR)-DLTS (ICTS) method.

Here, the outline of the conventional DLTS method will be briefly described with reference to FIGS. 11 to 15.

The DLTS method is a signal processing method that analyzes a change in the transient capacitance of the semiconductor 6 with respect to the pulse excitation using the electrical exciting means such as a bias voltage while sweeping a temperature in a prescribed range. The transient response of the capacitance of the semiconductor 6 at each measured temperature is represented as a graph such as indicated by each solid line in FIG. 11, for example. In each of such graphs, assuming that a difference in capacitance at prescribed time instants $t_1$ and $t_2$ in a measurement time is $S(T)$, $S(T)$ can be represented by the following expression (1):

$$S(T) = \{C(t_1, T) - C(t_2, T)\} \quad (1)$$

Figure 12:
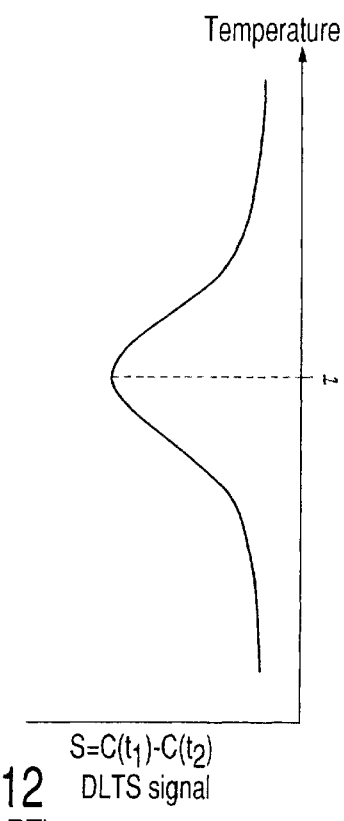
FIG. 12 is a view showing a DLTS signal of a given semiconductor based on the principle of the DLTS method according to the prior art in the form of a graph.

Plotting $S(T)$ with respect to each measurement temperature, a graph such as shown in FIG. 12 can be obtained. This graph shows a DLTS spectrum at each measurement temperature represented by the following expression (2), namely, a DLTS signal S:

$$S = C(t_1) - C(t_2) \quad (2)$$

The DLTS signal S represented by the graph shown in FIG. 12 has an extreme value at a temperature having a time constant $\tau$ represented by the following expression (3):

$$\tau = (t_1 - t_2)/\ln(t_1/t_2) \quad (3)$$

That is, the difference $S(T)$ in capacitance at each measurement temperature has an extreme value at each temperature represented by each time constant $\tau$, and each extreme value corresponds to one deep level at each measurement temperature of the semiconductor 6.

Figure 13:
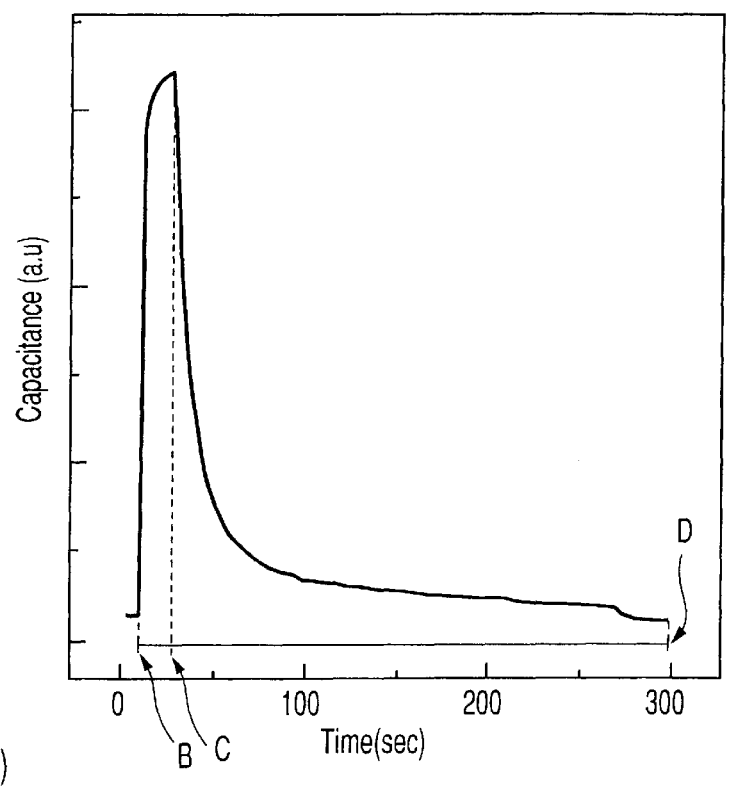
FIG. 13 is a view showing the time dependency of a change in the transient capacitance of a semiconductor by the DLTS method according to the prior art.
Figure 18:
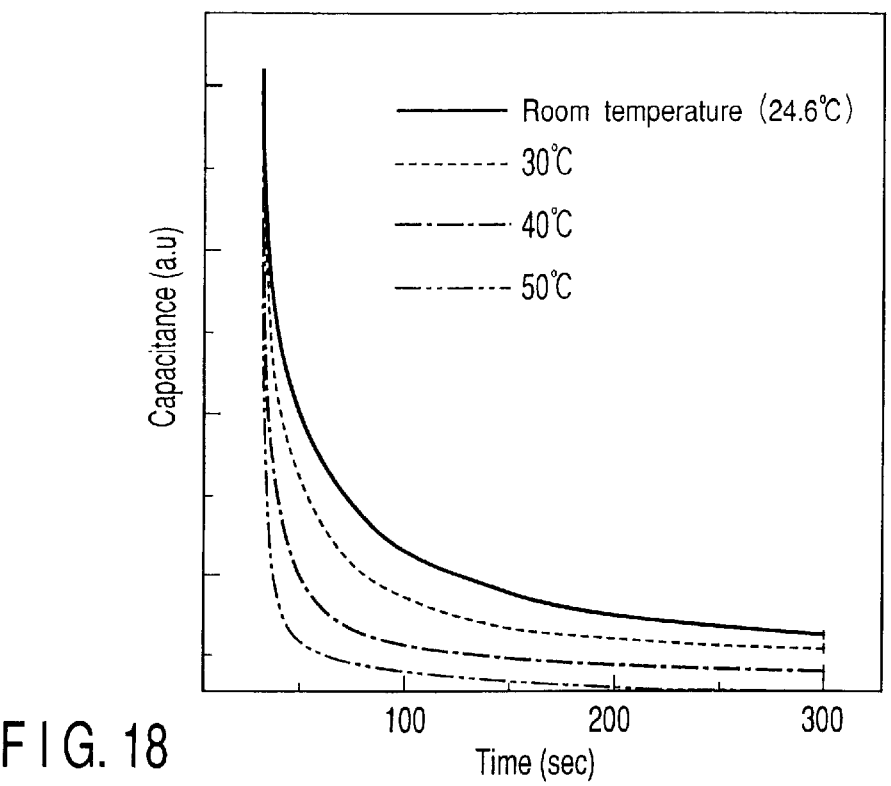
FIG. 18 is a view showing the time dependency of changes in the transient capacitance of a semiconductor at each temperature by the SR-DLTS method according to an aspect according to the present invention in the form of a graph.

A change in the transient capacitance of the semiconductor 6 with respect to the measurement time can be represented by a graph such as indicated by a solid line in FIG. 13. A time range indicated by B to C in FIG. 13 which is a rising part in the graph shows the state that the junction capacitance of the semiconductor 6 is temporarily increased when the carrier excited from the valence band in the normal state is trapped at a trapping level having a prescribed energy level existing between the valence band and the conduction band as shown in FIG. 14. Further, a part indicated by C in FIG. 13 shows that the density of the hole and the electron generated in the semiconductor 6 per unit volume becomes maximum value and the junction capacitance of the semiconductor 6 reaches a maximum value. Furthermore, a time range indicated by C to D in FIG. 13 which is an attenuating part in the graph shows the state that the carrier trapped at a trapping level is emitted from the trapping level by thermal excitation or the like and returns to the valence band at the energy level lower than the trapping level, and the junction capacitance of the semiconductor 6 is thereby decreased.

The specific procedure of the SR-DLTS method will now be schematically described with reference to a flowchart of FIG. 16.

A range of the wavelength of the intermittent X-ray beam used for measuring the transient response and a range of the measurement temperature when measuring the wavelength are first set, respectively. As to the wavelength of the intermittent X-ray beam, for example, a minimum wavelength λmin as a measurement start wavelength, a graduation range (step range) Δλ, and a maximum wavelength λmax as a measurement end wavelength are set, respectively. Similarly, as to the range of the measurement temperature, a minimum temperature Tmin as a measurement start temperature, a graduation range (step range) Δλ, and a maximum temperature Tmax as a measurement end temperature are set, respectively. Thereafter, measurement of the transient response of the semiconductor 6 is started by inputting the measurement start wavelength λmin and the measurement start temperature Tmin.

For example, the intermittent X-ray beam is applied toward the diode 2 for approximately 20 seconds in accordance with each measurement while maintaining the wavelength of the intermittent X-ray beam to λmin. When the measurement temperature T reaches the measurement end temperature Tmax or exceeds the measurement end temperature Tmax by increasing the measurement temperature by each graduation range Δλ every time one measurement is completed, measurement of the transient response of the semiconductor 6 with the measurement wavelength λ min is terminated. Subsequently, after increasing the measurement wavelength λ from λ min by the graduation width Δλ, similar measurement is carried out by increasing the measurement temperature from Tmin to the measurement end temperature Tmax in accordance with each graduation range ΔT. Thereafter, the transient response of the semiconductor 6 is measured while sequentially updating the measurement wavelength λ and the measurement temperature T. When the measurement wavelength λ reaches the measurement end wavelength λ max or exceeds the measurement end wavelength λ max, the SR-DLTS method is terminated.

Incidentally, if there is no enough time to perform the SR-DLTS method, it is good enough to conduct a so-called SR-ICTS method which holds the measurement temperature T at a prescribed temperature and measures the transient response of the semi-conductor 6 as shown in the flowchart of FIG. 17.

FIGS. 18 to 22 show the result of measuring and analyzing electrical properties of the diode 2 based on the SR-DLTS method. The time dependency of a change in the transient capacitance of the semiconductor 6 provided in the diode 2 at each measurement temperature in the vicinity of the K absorption edge of the Ga atom can be represented as in each graph in FIG. 18. Based on each graph, it can be understood that the time constant τ of a change in the transient capacitance of the semiconductor 6 is accelerated as the measurement temperature is increased. Moreover, the temperature dependency of the DLTS signal of the semiconductor 6 is represented as in each graph in FIG. 19. Although not shown, by applying peak fitting to each graph, it can be realized that the transient response of the semiconductor 6 corresponds to emit of one hole from a deep level at near a room temperature.

Figure 19:
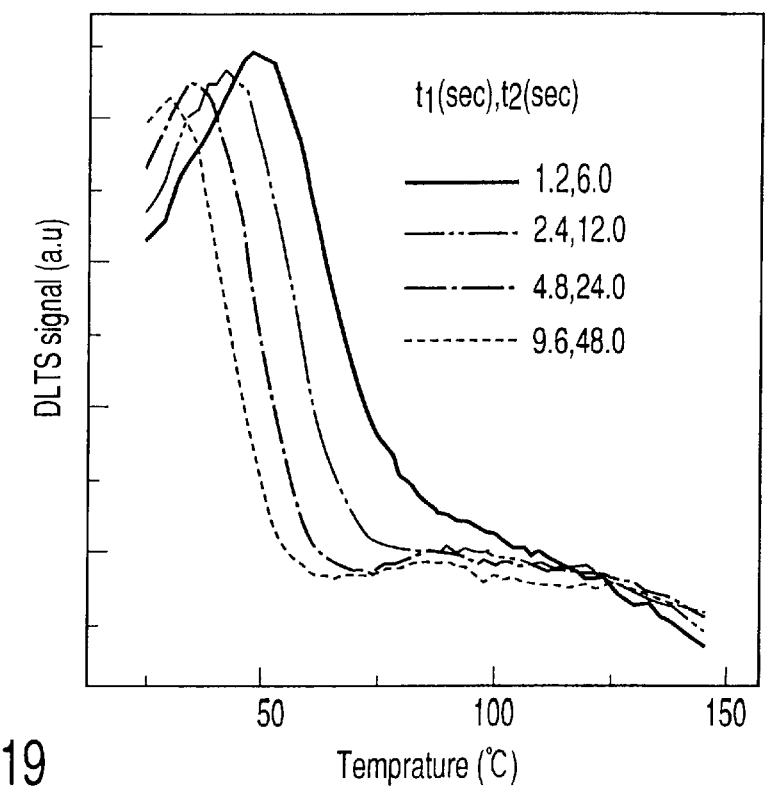
FIG. 19 is a view showing the temperature dependency of a DLTS signal indicative of changes in the transient capacitance of the semiconductor by the SR-DLTS method according to an aspect of the present invention in the form of a graph.
Figure 20:
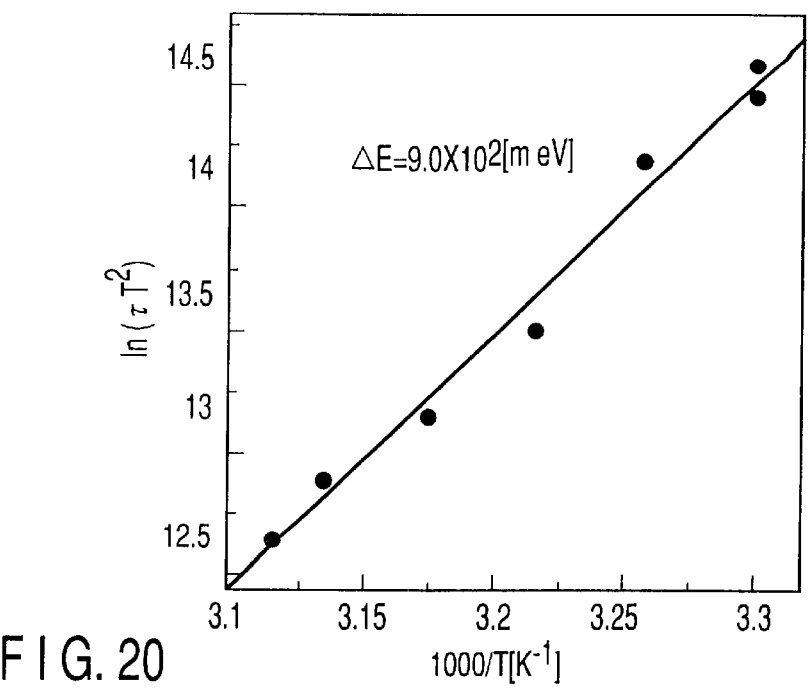
FIG. 20 is a view showing the temperature dependency of an emission rate of the semiconductor by the SR-DLTS method according to an aspect of the present invention in the form of a graph.
Figure 21:
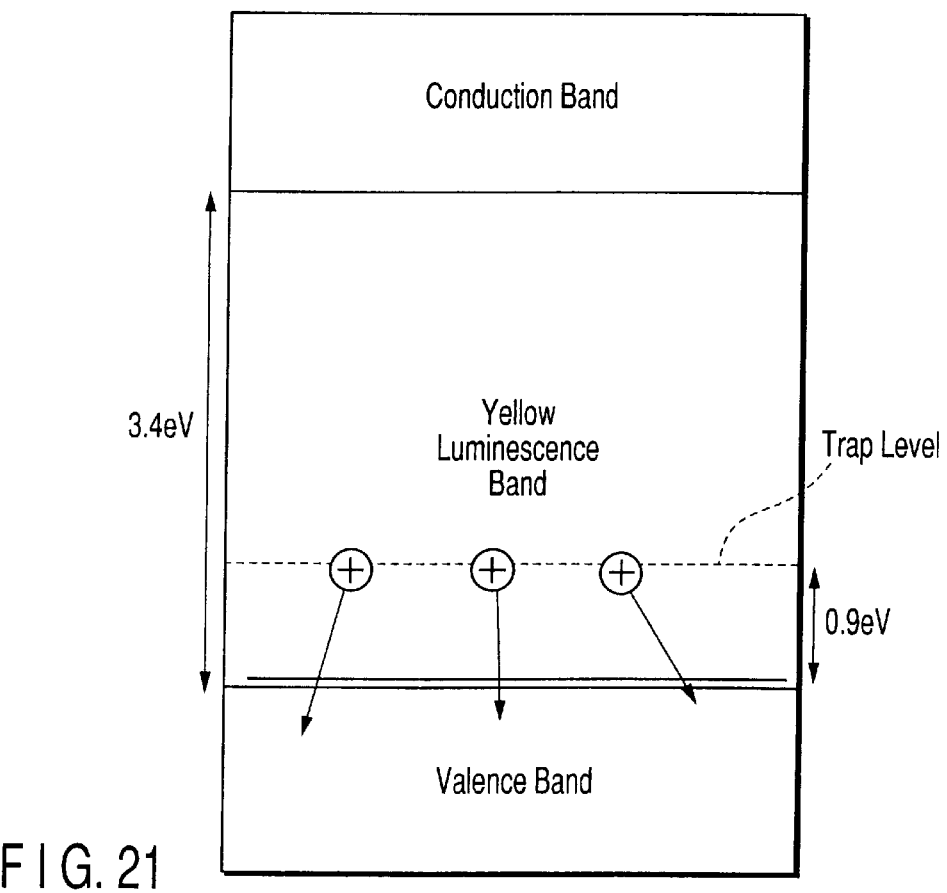
FIG. 21 is a view typically showing a trapping level of a carrier of the semiconductor by the SR-DLTS method according to an aspect of the present invention.

In addition, FIG. 20 shows a result of calculating an emission rate of the hole that is the carrier of the semiconductor 6 from a peak in each graph in FIG. 19 and plotting its temperature dependency. Consequently, it can be understood that the depth of the trapping level at which the hole of the conductor is trapped in the excited state is placed at a position where the energy level is higher than the top part, where the energy level in the valence band is shallowest, by approximately 0.9 eV. As shown in FIG. 21, the position (depth) of the trapping level substantially matches with the impurity level to which the Ga hole relates, which exists in a range of approximately 3.4 eV between the valence band and the conduction band of the semiconductor 6 and is generally called a yellow luminescence band.

Figure 22:
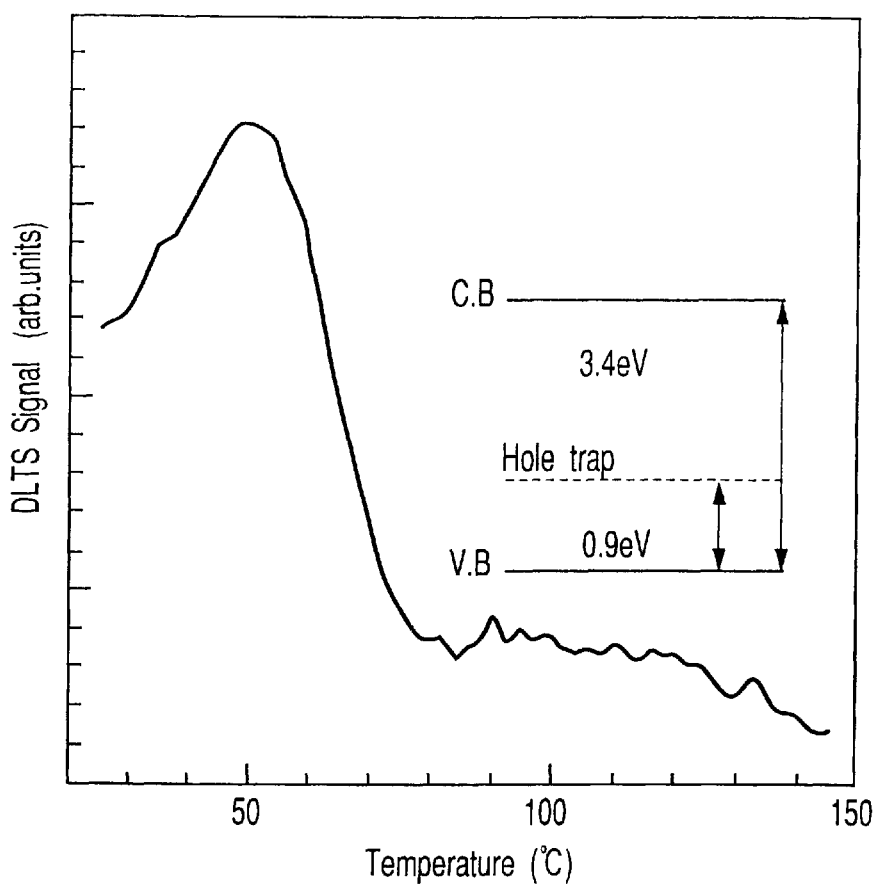
FIG. 22 is a view showing the temperature dependency of a DLTS signal indicative of changes in the transient capacitance and a trapping level of a carrier of the semiconductor by the SR-DLTS method according to an aspect of the present invention.

FIG. 22 shows the sum-up of the results mentioned above. Although not shown, this result substantially corresponds to the result obtained by measuring and analyzing electrical properties of the diode 2 by the conventional DLTS method. As a result, it can be understood that information concerning electrical properties of the diode 2 obtained by the SR-DLTS method has the high accuracy which is reliable as with information obtained by the prior art DLTS method. Thus, according to the evaluation method of this aspect including the SR-DLTS method, electrical properties of the diode 2 can be evaluated with the high accuracy.

Further, among the evaluation methods according to this aspect, the method for evaluating structural characteristics and electron states or the like of the diode 2 is similar to the XAFS method according to the prior art. Therefore, the detailed description concerning its specific procedure is omitted, and only its result will be illustrated and explained. The XAFS method according to this aspect measures and analyzes the energy spectrum of the continuous X-ray beam 3 absorbed in an element present in the semiconductor 6 by continuously applying the X-ray beam 3 to the diode 2 with by using the evaluation apparatus 1, and evaluates the structure and electron states of the semiconductor 6.

Figure 23:
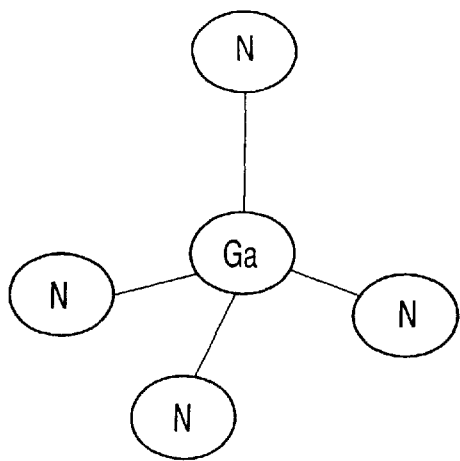
FIG. 23 is a view typically showing a local structure in a vicinity of a Ga atom in a regular crystal by the XAFS method executed by an evaluation method according to an aspect of the present invention.
Figure 24:
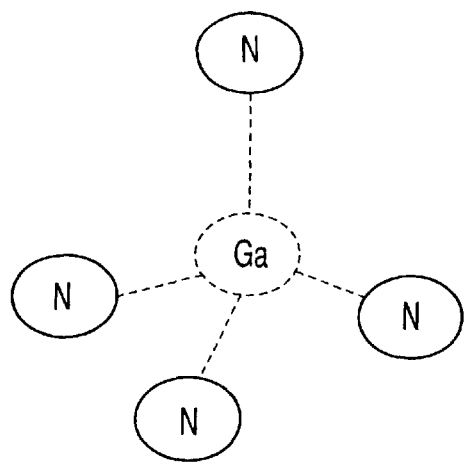
FIG. 24 is a view typically showing a local structure in a vicinity of a Ga atom when the Ga atom is a hole by the XAFS method executed by the evaluation method according to an aspect of the present invention.

The local structure of the Ga atom in the regular crystal can be typically shown in FIG. 23. However, the capacitance XAFS signal indicative of a result of the structure analysis of the diode 2 according to the XAFS method clearly represents that the Ga atom does not relate to defects in the semiconductor 6 as indicated by a solid line in FIG. 9. As indicated by a broken line in FIG. 24, it can be considered that there is substantially no difference between the capacitance XAFS signal and the fluorescent XAFS signal in the vicinity of the K absorption edge because the Ga atom from which defects can originate is a hole. This can be consistent with the fact that the depth of the level at which the hole of the semiconductor 6 is trapped is substantially matched with the yellow luminescence band, which is a result obtained by the SR-DLTS method.

As described above, by performing the SR-DLTS method and the XAFS method according to this aspect, it is possible to obtain the result supporting the theory that the level at which the hole of the semiconductor 6 is trapped arises from $V_{Ga}$. Furthermore, applying the SR-DLTS method to the diode 2 can detect the deep level that is called the yellow luminescence band. According to this detection sensitivity, a change in the junction capacitance of the semiconductor 6, which is approximately 1/100, can be readily detected. For example, assuming that the concentration of the donor or the acceptor is 1E15, the deep level having the concentration of 1E13 can be easily detected, and the deep level having the concentration of 1E12 can be likewise successfully detected. Moreover, since the X-ray beam can sufficiently reach to a deep position in the structure of the semiconductor 6, the structure buried in a deep position inside the diode 2 can be accurately and readily measured and analyzed. By appropriately changing the intensity of the energy or the wavelength of the X-ray beam 3, it is possible to be aware of structural characteristics of the atomic scale at a depth corresponding to these intensity and wavelength.

The evaluation method according to this aspect utilizes quantities of the X-ray beam in the various states such as a temperature, a wavelength of the X-ray beam, the intensity of the energy or the like as main parameters. In the experiment mentioned above, the Au/n type GaN Schottky diode 2 having the known electrical properties or the structural information and electron states of the semiconductor 6 is determined as a target of evaluation. Therefore, although the structural information and electron states of the diode 2 are first measured and analyzed by the XAFS method, electrical properties of the diode 2 may be first measured and analyzed by the SR-DLTS method. Specifically, a temperature at which a signal concerning a specific defect existing in the semiconductor 6 is generated is first obtained. Then, the structural information and electron states of the semiconductor 6 are measured by changing the wavelength of the X-ray beam 3 and the intensity of the energy at that temperature. As a result, there is obtained information concerning electrical properties or the structural information and electron states relating to a specific defect in the semiconductor 6. Subsequently, electrical properties of the semiconductor 6 is repeatedly measured and analyzed by changing a measurement temperature, the wavelength of the X-ray beam and the intensity of the energy or the like. Consequently, it is possible to be aware of the further detailed electrical properties based on structural characteristics of the semiconductor 6.

As described above, according to the evaluation method for the semiconductor device of the aspect of the present invention, the intermittent X-ray beam in the form of the pulse applied light can be utilized as an excitation source when evaluating electrical properties of the semiconductor device. In addition, electrical properties of the semiconductor 6 and the microscopic structure of the semiconductor 6 or the like can be easily evaluated with the high accuracy of the atomic scale in the site selection manner by switching the continuous application mode or the intermittent application mode of the X-ray beam. Therefore, according to the evaluation method of the present invention, the correlation between electrical properties of the semiconductor device, the fine structure and electron states in the semiconductor can be readily resolved with the high reliability irrespective of a part or a material to be measured in the semiconductor device 2, which has been conventionally considered almost impossible.

Additionally, the evaluation method according to this aspect reveals the correlation of electrical properties of the diode 2 and the structural information of the diode 2 or the like with the high accuracy by alternately repeating measurement and analysis of electrical properties of the diode 2 and measurement and analysis of the structural information of the diode 2. Therefore, when conducting the evaluation method according to this aspect, it is practically preferable to use the one evaluation apparatus 1 capable of performing the SR-DLTS method and the XAFS method or the like. In particular, in order to eliminate measurement errors due to a change in the measurement environment as much as possible and rapidly, accurately and readily perform the evaluation method according to this aspect, use of the evaluation apparatus 1 is substantially integrant.

It is to be noted that the evaluation method and the evaluation apparatus for the semiconductor device according to the present invention are not restricted to the aspect mentioned above. They can be carried out by changing a part of, e.g., the steps or the structure to various kinds of settings or incorporating various kinds of settings without departing from the scope of the present invention.

For example, improving the sensitivity of the X-ray detector 10 can carry out the XAFS method of the evaluation method according to the present invention even if a small X-ray structure analysis apparatus is used in place of the synchrotron 14. Further, in order to further improve the noise reduction effect of the evaluation apparatus 1, the shielded cable 18 may be used instead of the connection cable 26 for connecting the computer 9 (12) with the synchrotron 14 or the X-ray beam chopper 5*a*. Furthermore, the first A/D converter 19*a* to the third A/D converter 19*c* may be integrated with the computer 9 (12), respectively.

Moreover, a temperature adjustment device capable of adjusting an ambient temperature of the entire X-ray optical system may be provided.

In addition, it is good enough that the size, the shape and a number of the X-ray beam passing holes 15*a* and the X-ray beam interception holes 15*b* of the X-ray beam chopper 5*a* are formed in such a manner that the semiconductor device 2 can be appropriately and accurately evaluated. Even if the rotor plate 15 is rotated at an equal speed by using a plurality of the rotor plate 15 formed so as to obtain application mode different from each other, the application mode of the X-ray beam 3 can be further finely set in accordance with the structure of the semiconductor device 2 or the desired evaluation accuracy.

Additionally, in the evaluation method according to the present invention, either electrical properties or the structure of the semiconductor device 2 can be measured and analyzed before. Further, according to the present invention, it is possible to evaluate not only the semiconductor 6 comprising the semiconductor device 2 but also electrical properties and the structure of, e.g., an insulator. Furthermore, by applying the evaluation method according to the present invention in each step in the manufacturing process of the semiconductor device 2 by utilizing the evaluation apparatus 1 according to the present invention, it is possible to readily detect a step on which a defect or a hole was generated, or its origin. Moreover, by shortening the wavelength of the X-ray beam and narrowing down its diameter, the evaluation apparatus 1 can be used as an X-ray microscope having the higher resolution than a regular photon microscope utilizing a visible light ray.

Additional advantages and modifications will readily occur to those skilled in the art. Therefore, the invention in its broader aspects is not limited to the specific details and representative aspects shown and described herein. Accordingly, various modifications may be made without departing from the spirit or scope of the general inventive concept as defined by the appended claims and their equivalents.

What is claimed is:

1. A method for evaluating a semiconductor device, comprising the steps of:

evaluating electrical properties of a semiconductor device by measuring and analyzing a junction capacitance of a semiconductor provided in the semiconductor device and a transient change of the junction capacitance while applying an X-ray beam to the semiconductor device intermittently; and evaluating a structure and electron states of the semiconductor by measuring and analyzing an energy spectrum of an X-ray beam absorbed into an element present in the semiconductor while applying an X-ray beam to the semiconductor device continuously.

2. The method according to claim 1, further comprising the steps of:

switching a mode of applying the X-ray beam to the semiconductor device, between an intermittent application mode and a continuous application mode, in accordance with an evaluating purpose for the semiconductor device; and adjusting an applying time of the X-ray beam to the semiconductor device in accordance with an evaluating accuracy of the semiconductor.

3. The method according to claim 1, further comprising the step of:

adjusting a wavelength, energy, and diameter of the X-ray beam in accordance with an evaluating accuracy of the semiconductor.

4. The method according to claim 1, further comprising the steps of:
   adjusting a temperature of the semiconductor device; and
   maintaining the temperature of the semiconductor device at prescribed values while the junction capacitance and the transient change of the junction capacitance are being measured.

5. The method according to claim 2, further comprising the step of:
   adjusting a wavelength, energy, and diameter of the X-ray beam in accordance with an evaluating accuracy of the semiconductor.

6. The method according to claim 2, further comprising the steps of:
   adjusting a temperature of the semiconductor device; and
   maintaining the temperature of the semiconductor device at prescribed values while the junction capacitance and the transient change of the junction capacitance are being measured.

7. The method according to claim 3, further comprising the steps of:
   adjusting a temperature of the semiconductor device; and
   maintaining the temperature of the semiconductor device at prescribed values while the junction capacitance and the transient change of the junction capacitance are being measured.

8. The method according to claim 5, further comprising the steps of:
   adjusting a temperature of the semiconductor device; and
   maintaining the temperature of the semiconductor device at prescribed values while the junction capacitance and the transient change of the junction capacitance are being measured.

9. An apparatus for evaluating a semiconductor device, comprising:
   an X-ray beam applying device which applies an X-ray beam to a semiconductor device;
   an X-ray beam application-time setting device which switches a mode of applying the X-ray beam to the semiconductor device, between an intermittent application mode and a continuous application mode, and which sets an X-ray beam application-time to prescribed values;
   a junction capacitance detecting device which detects a junction capacitance of a semiconductor provided in the semiconductor device and a transient change of the junction capacitance while the X-ray beam is being intermittently applied to the semiconductor device;
   a junction capacitance measurement device which measures the junction capacitance and the transient change thereof, both detected by the junction capacitance detecting device;
   a first evaluation device which analyzes the junction capacitance and the transient change thereof, both measured by the junction capacitance measurement device and which evaluates electrical properties of the semiconductor device;
   an X-ray spectrum detecting device which detects an energy spectrum of the X-ray beam continuously applied to and absorbed into an element present in the semiconductor, while the X-ray beam is being continuously applied to the semiconductor device;
   an X-ray spectrum measurement device which measures the energy spectrum detected by the X-ray beam spectrum detecting device; and
   a second evaluation device which analyzes the energy spectrum measured by the X-ray beam spectrum measurement device and which evaluates a structure and electron states of the semiconductor device.

10. The apparatus according to claim 9, wherein the X-ray beam application-time setting device synchronizes the switching of the mode of applying the x-ray beam and the application of the X-ray beam with detection and measurement of the junction capacitance and the transient change thereof or with detection and measurement of the energy spectrum of the X-ray beam continuously applied to and absorbed into an element present in the semiconductor.

11. The apparatus according to claim 9, wherein the X-ray beam applying device sets a wavelength, energy, and diameter of the X-ray beam, independently, to prescribed values.

12. The apparatus according to claim 9, further comprising:
   a temperature adjustment device which sets a temperature of the semiconductor device to prescribed values.

13. The apparatus according to claim 9, further comprising:
   a noise reduction device which reduces noises generated while detecting and measuring the junction capacitance and the transient change thereof, and reduces noises generated while detecting and measuring the energy spectrum of the X-ray beam continuously applied to and absorbed into an element present in the semiconductor.

14. The apparatus according to claim 10, wherein the X-ray beam applying device sets a wavelength, energy, and diameter of the X-ray beam, independently, to prescribed values.

15. The apparatus according to claim 10, further comprising:
   a temperature adjustment device which sets a temperature of the semiconductor device to prescribed values.

16. The apparatus according to claim 10, further comprising:
   a noise reduction device which reduces noises generated while detecting and measuring the junction capacitance and the transient change thereof, and reduces noises generated while detecting and measuring the energy spectrum of the X-ray beam continuously applied to and absorbed into an element present in the semiconductor.

17. The apparatus according to claim 11, further comprising:
   a temperature adjustment device which sets a temperature of the semiconductor device to prescribed values.

18. The apparatus according to claim 11, further comprising:
   a noise reduction device which reduces noises generated while detecting and measuring the junction capacitance and the transient change thereof, and reduces noises generated while detecting and measuring the energy spectrum of the X-ray beam continuously applied to and absorbed into an element present in the semiconductor.

19. The apparatus according to claim 12, further comprising:
   a noise reduction device which reduces noises generated while detecting and measuring the junction capacitance and the transient change thereof, and reduces noises generated while detecting and measuring the energy spectrum of the X-ray beam continuously applied to and absorbed into an element present in the semiconductor.

20. The apparatus according to claim 14, further comprising:
a temperature adjustment device which sets a temperature of the semiconductor device to prescribed values.

21. The apparatus according to claim 14, further comprising:
a noise reduction device which reduces noises generated while detecting and measuring the junction capacitance and the transient change thereof, and reduces noises generated while detecting and measuring the energy spectrum of the X-ray beam continuously applied to and absorbed into an element present in the semiconductor.

22. The apparatus according to claim 15, further comprising:
a noise reduction device which reduces noises generated while detecting and measuring the junction capacitance and the transient change thereof, and reduces noises generated while detecting and measuring the energy spectrum of the X-ray beam continuously applied to and absorbed into an element present in the semiconductor.

23. The apparatus according to claim 17, further comprising:
a noise reduction device which reduces noises generated while detecting and measuring the junction capacitance and the transient change thereof, and reduces noises generated while detecting and measuring the energy spectrum of the X-ray beam continuously applied to and absorbed into an element present in the semiconductor.

24. The apparatus according to claim 20, further comprising:
a noise reduction device which reduces noises generated while detecting and measuring the junction capacitance and the transient change thereof, and reduces noises generated while detecting and measuring the energy spectrum of the X-ray beam continuously applied to and absorbed into an element present in the semiconductor.

* * * * *